United States Patent
Lee (10) Patent No.: US 12,153,010 B2
(45) Date of Patent: Nov. 26, 2024

(54) MULTIWELL ELECTRODE-BASED BIOSENSOR

(71) Applicant: Korea Research Institute of Chemical Technology, Daejeon (KR)

(72) Inventor: Kyuhong Lee, Jeollabuk-do (KR)

(73) Assignee: KOREA RESEARCH INSTITUTE OF CHEMICAL TECHNOLOGY, Deajeon (KR)

( * ) Notice: Subject to any disclaimer, the term of this patent is extended or adjusted under 35 U.S.C. 154(b) by 854 days.

(21) Appl. No.: 17/048,002

(22) PCT Filed: Apr. 10, 2019

(86) PCT No.: PCT/KR2019/004259
§ 371 (c)(1),
(2) Date: Oct. 15, 2020

(87) PCT Pub. No.: WO2019/203493
PCT Pub. Date: Oct. 24, 2019

(65) Prior Publication Data
US 2021/0140912 A1    May 13, 2021

(30) Foreign Application Priority Data
Apr. 17, 2018 (KR) .................. 10-2018-0044218

(51) Int. Cl.
*G01N 27/327* (2006.01)
*G01N 33/543* (2006.01)
*G01N 33/68* (2006.01)

(52) U.S. Cl.
CPC ..... *G01N 27/3277* (2013.01); *G01N 27/3276* (2013.01); *G01N 27/3278* (2013.01); *G01N 33/5438* (2013.01); *G01N 33/68* (2013.01)

(58) Field of Classification Search
CPC ........... G01N 27/3277; G01N 27/3276; G01N 33/5438; G01N 33/68
See application file for complete search history.

(56) References Cited

U.S. PATENT DOCUMENTS 6,391,558 B1 * 5/2002 Henkens ............. C12Q 1/6825
  422/50
6,770,190 B1   8/2004 Milanovski et al.
(Continued)

FOREIGN PATENT DOCUMENTS

CN     101400800 A     4/2009
CN     105929153 B     8/2017
(Continued)

OTHER PUBLICATIONS

Lee et al., "Well-oriented nanowell array metrics for integrated digital nanobiosensors," Applied Physics Letters 89, 113901 (2006) (Year: 2006).*
EPO machine-generated English language translation of Park et al. KR 20140081208 A (Year: 2014).*
Lorimer et al., "Enhanced Chemiluminescence: A High-sensitivity Detection System for In Situ Hybridization and Immunohistochemistry," The Journal of Histochemistry and Cytochemistry vol. 412, No. 11, pp. 1591-1597, 1993 (Year: 1993).*
(Continued)

Primary Examiner — Alexander S Noguerola
(74) Attorney, Agent, or Firm — CANTOR COLBURN LLP (57) ABSTRACT

The present invention relates to a multiwell electrode-based biosensor, which, by using amperometry, can have a reduced size compared to existing biosensors that use impedance measurement and, by incorporating immunoassay methods, shows sensitivity to the level of fg/ml and thus can effectively detect a target protein comprised, in blood, in an extremely small amount. Probes which are different from one another are comprised in multiple wells and thus various target proteins can simultaneously be detected by means of a single procedure.

6 Claims, 8 Drawing Sheets

(56) References Cited

U.S. PATENT DOCUMENTS

| 10,386,321 | B2 | 8/2019 | LaBelle et al. |
| 2007/0231794 | A1 | 10/2007 | Dill et al. |
| 2017/0219554 | A1 | 8/2017 | Lee |

FOREIGN PATENT DOCUMENTS

| JP | 2002533698 | A | 10/2002 |
| JP | 2005164388 | A | 6/2005 |
| JP | 2009510485 | A | 3/2009 |
| JP | 4774150 | B2 | 7/2011 |
| JP | 2017524137 | A | 8/2017 |
| KR | 100601999 | B1 | 7/2006 |
| KR | 1006019990000 | B1 | 7/2006 |
| KR | 1020070053545 | A | 5/2007 |
| KR | 1020130121464 | A | 11/2013 |
| KR | 1020140081208 | A | 7/2014 |
| KR | 1020150118894 | A | 10/2015 |

OTHER PUBLICATIONS

English language version of the Written Opinion for international application No. PCT/KR2019/004259, dated Jun. 7, 2019 (Year: 2019).*
English Abstract of CN105929153.
English Abstract of JP 2002-533698.
English Abstract of JP 2017-524137.
English Abstract of JP 4774150.
English Abstract of KR 10-0601999.
Extended European Search Report issued in corresponding EP Patent Application No. 19787864.8, dated Apr. 1, 2022.
Lee Jukyung et al: "Wafer-scale nanowell array patterning based electrochemical impedimetric immunosenser", Journal of Biotechnology 168 (2013) 584-588.
Seo Youngtae et al: "Innovations in biomedical nanoengineering: nanowell array biosensor", Nano Convergence (2018) 5:9, 18 pp.

* cited by examiner

MULTIWELL ELECTRODE-BASED BIOSENSOR

CROSS REFERENCE TO RELATED APPLICATIONS

This application is a National Stage application of PCT/KR2019/004259, filed Apr. 10, 2019, which claims the benefit of Korean Application No. 10-2018-0044218, filed Apr. 17, 2018, both of which are incorporated by reference in their entirety herein.

TECHNICAL FIELD

The present invention relates to a multiwell based-biosensor with improved sensitivity in detecting a very small amount of a target substance.

BACKGROUND

Recently, biosensors have received a lot of attention in the fields of screening processes for the development of new drugs, disease diagnosis, and so on by using micro-samples, leading to active research and development thereof in progress. In particular, the development of small biosensors has progressed a lot for quickly and accurately measuring on-site the presence or concentration of a trace amount of target substances present in sample solutions such as blood, urine, saliva, and the like, and examples include biospecific binding, immune sensors, DNA sensors, etc.

The enzyme-linked immunosorbent assay (ELISA) method is mainly used conventionally to measure proteins, which is a method of quantifying a trace amount of antigen protein, by immobilizing an antibody on a support, reacting a sample solution in which the antigen protein is mixed to the surface on which the antibody is immobilized for a predetermined period of time, followed by binding a detection antibody that selectively binds to the antigen protein onto the surface to which the antigen protein is bound, and then binding an enzyme to the detection antibody and adding a reactant capable of causing the enzyme to develop a color or fluorescence property, resulting in a color or fluorescence reaction. The ELISA method has been used to date to effectively measure a trace amount of antigen proteins; however, since the analysis range of antigen proteins is small and only one protein can be analyzed at a time, there is a drawback in that a large amount of sample (200 ul) is needed and accurate measurement is difficult in the concentration of pg/ml level.

Thus, methods for conveniently measuring the concentration of an antigen through a process applied to a biosensor and biochip by using the principle of the ELISA have been developed lately. As examples, there are research results measured with surface plasmon resonance (SPR), quartz crystal microbalances, electrochemical sensors, and so on. These methods have the advantage of being able to conveniently detect a very small amount of a target substance present in a sample, as well as to simultaneously detect various types of antigens. However, the above method exhibits a result that the sensitivity is not significantly improved compared to the ELISA method, and thus there is a need for research and development for biosensors with improved sensitivity in detecting a very small amount of a target substance.

In addition, cytokines such as TNF-alpha, TGF-beta, IFN-gamma, and the like are generally measured to determine lung damage caused by inhalation of harmful substances and cardiovascular damage resulting therefrom; however, since cytokines exist at an extremely low concentration of 10 to 400 pg/ml in the blood, causing the sensing to be difficult, and thus there is a need for research and development for biosensors with improved sensitivity.

SUMMARY OF INVENTION

Technical Objects

It is an object of the present invention to provide a multiwell biosensor.

It is another object of the present invention to provide a method of detecting a target substance in a sample using the biosensor.

It is yet another object of the present invention to provide a method of manufacturing the biosensor in accordance with the present invention.

However, technical objects to be achieved by the present invention are not limited to those mentioned above, and other objects that have not been mentioned will be clearly understood by those of ordinary skill in the art from the following description.

Technical Solution

There is provided an electrochemical biosensor comprising: an electrode in which one or more wells for accommodating a sample are formed; a first probe on the electrode and an adaptor protein that specifically binds to the first probe; a second probe that specifically binds to a target substance that binds to the first probe; and a signal mediator molecule that specifically binds to the second probe.

Further, in the present invention, the electrochemical biosensor may measure a concentration of the target substance in the sample by an amperometry method.

In addition, in the present invention, the adaptor protein to be bound to the electrode may bind to the electrode so as to exist within the well.

Furthermore, in the present invention, the first probe may specifically bind to the adaptor protein immobilized on the electrode exposed at a bottom portion of the well.

Moreover, in the present invention, the electrode may be surface-modified into a self-assembled monolayer (SAM).

In addition, in the present invention, the second probe may be bound to a protein tag, and the signal mediator molecule may be bound to a peroxidase.

Further, in the present invention, the signal mediator molecule may be bound to the protein tag of the second probe.

Moreover, in the present invention, the protein tag may be one or more selected from the group consisting of biotin, calmodulin, FLAG, His, Myc, and streptavidin binding protein (SBP).

In addition, in the present invention, the target substance may be a protein or peptide.

Another implementation of the present invention provides a method of detecting a target substance in a sample using an electrochemical biosensor, wherein the electrochemical biosensor comprises an electrode in which one or more wells for accommodating a sample are formed, a first probe provided at a bottom portion of the well, and an adaptor protein that specifically binds to the first probe, the method comprising:

a) placing and reacting a biological sample separated from an object in the electrochemical biosensor;

b) providing and reacting a second probe targeting a target substance to the well;

c) reacting a signal mediator molecule targeting a substance tagging the second probe to the well; and d) by the reaction between the second probe and the signal mediator molecule in said step c) in the presence of an electrolyte, measuring an electric current generated by a redox reaction.

Moreover, in the present invention, the electrolyte in said step d) may comprise one or more of TMB (3,3',5,5'-Tetramethylbenzidine), ECL (Enhanced chemiluminescence), and Hydroquinone.

Effects of the Invention

The biosensor in accordance with the present invention can be made smaller in size by using amperometry compared to existing biosensors that use impedance measurement and can exhibit sensitivity in the order of fg/ml by incorporating immunoassay methods, and thus, can effectively detect a target protein contained in an extremely small amount in the blood.

Moreover, it is possible to simultaneously detect various target proteins through a single process by comprising different probes in each of a number of wells.

In addition, since a redox method in which a specific voltage is applied and then a current is measured is used, the analysis time is very short within 5 seconds.

DETAILED DESCRIPTION OF EMBODIMENTS

Hereinafter, preferred embodiments of the present invention will be described with reference to the accompanying drawings. However, embodiments of the present invention may be modified in various other forms, and the scope of the present invention is not limited to the embodiments described below. Furthermore, embodiments of the present invention are provided for a more complete description of the present invention to those having ordinary knowledge in the art.

The present inventors have found out that the sensitivity of measurement of a target substance in a sample can be significantly improved if a biosensor having an electrode in which wells of a cylindrical shape having a micro- or nano-size in diameter are formed includes a second probe to which a protein tag is attached and a signal mediator molecule capable of specifically binding to the second probe, as a result of efforts made to develop a biosensor with higher sensitivity in detecting a very small amount of a target substance contained in a sample in the conventional ELISA method, thereby completing the present invention.

Figure 15:
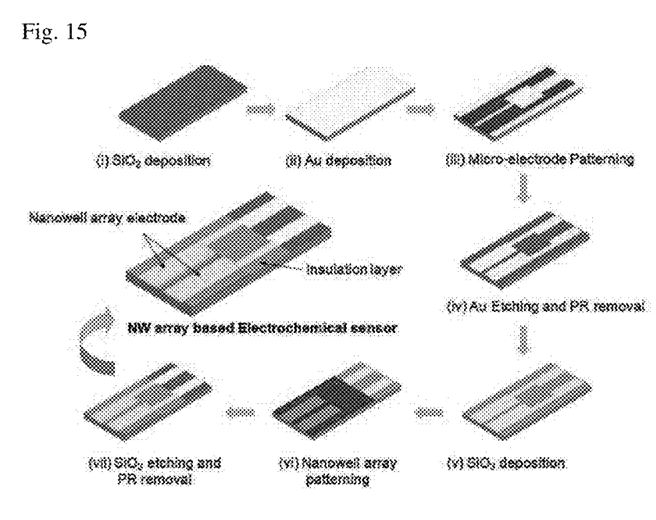
FIG. 15 shows a process of manufacturing a biosensor having a nanowell array electrode.

In the present invention, as an implementation, the biosensor may be a biosensor having a nanowell array electrode obtained through a manufacturing process in FIG. 15. In an example, currently known various methods of forming nanowells may be applied to the nanowells, and for example, a technique of patterning a nanowell structure on a silicon wafer base, and the like may be applied.

The present invention relates to an electrochemical biosensor comprising: an electrode in which one or more wells for accommodating a sample are formed; a first probe provided on the electrode and an adaptor protein that specifically binds to the first probe; a second probe that specifically binds to a target substance that binds to the first probe; and a signal mediator molecule that specifically binds to the second probe. Hereinafter, each constituent of the biosensor in accordance with the present invention will be described in detail with reference to the drawings.

Electrode 100 Comprising One or More Wells for Accommodating Sample:

This is an electrode wiring, corresponding to a constituent for detecting electrons generated in a sample to detect a target substance.

In the present invention, the electrode may be one or more of Cu, Ni, Fe, Pt, and Au, and may preferably be Au but is not limited thereto.

Figure 2:
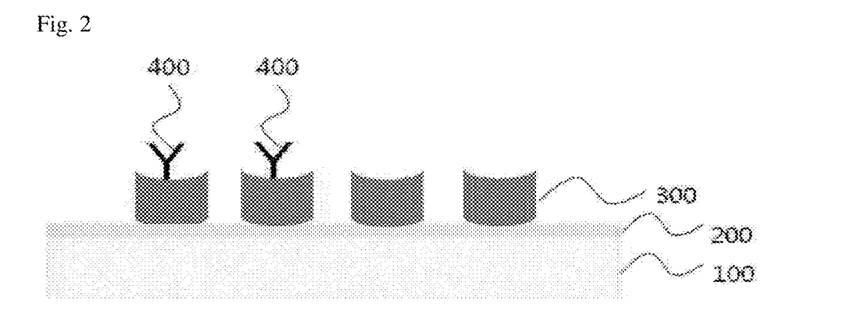
FIG. 2 shows a schematic diagram of a biosensor in accordance with an embodiment of the present invention.

As shown in FIG. 2, furthermore, a surface of the electrode in the present invention may be a modified surface 200 to facilitate the binding of the first probe and the adaptor protein. In particular, the modification of the surface may be modified into a self-assembled monolayer (SAM). In the case of modifying the surface of the electrode into a self-assembled monolayer, stability, reproducibility, and sensitivity can be significantly improved by stably inducing the covalent bond between the first probe 400 and the adaptor protein 300.

Figure 1:
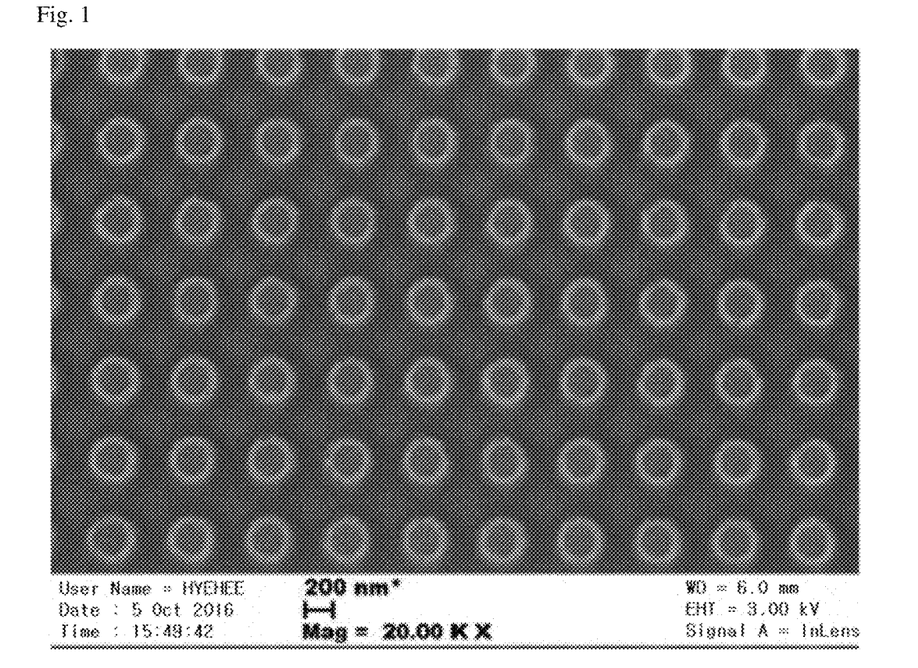
FIG. 1 shows a schematic diagram of wells having a nano-sized diameter of a biosensor in accordance with an embodiment of the present invention.

In addition, the one or more wells in the present invention may be of a well structure having a diameter of micro- to nano-size, and may be cylindrical wells, as shown in FIG. 1. As such, in the case of having a diameter of micro- to nano-size, it is possible to exhibit the effect of filtering out macromolecular proteins such as albumin, and so on other than the target substance contained in a biological sample separated from an intended object or obtained by other methods. Moreover, in the case of having the shape of a cylindrical well, it is possible to maximize the diffusion of electron transfer according to Equation (1) below, to thereby detect a very small amount of sample efficiently, compared to the case without such a shape.

$$I_{lim} = \frac{4\pi n F c^b D r^2}{4L + \pi r} \quad (1)$$

Preferably, the size of the wells may be 50 to 500 nm in diameter, or 200 to 500 nm in diameter, for example, 300 to 400 nm in diameter, but is not limited thereto. If the diameter of the cylindrical well is less than 50 nm, it may be difficult for the antibody to be immobilized in the well; if the diameter is less than 200 nm, it may be impossible to maximize the diffusion of electron transfer inside thereof for measurement; and if over 500 nm, it may not be able to sufficiently filter out unnecessary proteins other than the target substance.

First Probe and Adaptor Protein:

The adaptor protein corresponds to a constituent for facilitating the bonding between the electrode and the first probe 400 that first captures the target substance 500 present in the intended sample.

In the present invention, the first probe 400 may include all of the molecules capable of specifically binding to the target substance present in the sample, and, in particular, may be antibodies, proteins, other biomolecules, or the like that specifically bind to the target substance, but is not limited thereto.

Furthermore, the adaptor protein 300 in the present invention may include all of those capable of immobilizing the first probe such as an antibody, protein, and so on, and, in particular, may be protein A, protein G, streptavidin, or the like, but is not limited thereto. As such, if the first probe is bound to the adaptor protein without being directly bound to the electrode, it is possible to significantly increase the fixation efficiency between the first probe and the electrode and to reduce non-specific reactions.

Here, the "target substance 500" in the present invention may be a peptide or protein for measurement contained in a biological sample separated from an intended object.

In the present invention, the "peptide" includes a polypeptide, and the terms peptide, polypeptide, or protein refer to polymers of amino acid residues. Not only naturally occurring amino acids such as one or more amino acid residues but also analogs into which polymers of naturally occurring amino acids are artificially synthesized also fall within the scope of the present invention.

For the purposes of the present invention, the target substance may be a cytokine protein, which is a protein contained in a very small amount in a sample, and preferably, the cytokine protein may be interleukin, TGF-alpha, TGF-beta, interleukin-4, interleukin-6, MCP-1, interleukin-1-beta, interleukin-17, IFN-gamma, or the like.

Figure 3:
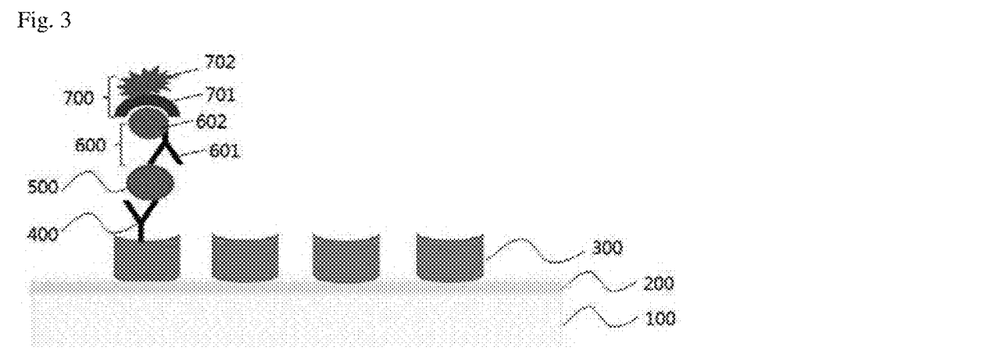
FIG. 3 shows a schematic diagram of a biosensor in accordance with an embodiment of the present invention.

As can be seen in FIG. 3, one embodiment of the present invention may relate to a biosensor further comprising a second probe that specifically binds to the target substance captured by the first probe and a signal mediator molecule that specifically binds to the second probe.

Second Probe:

It corresponds to a constituent that specifically binds to the target substance captured by the first probe.

In the present invention, the second probe 601 may include all of the molecules capable of specifically binding to the target substance 500, and, in particular, may be proteins, antibodies, and so on, but is not limited thereto. Moreover, the second probe in the present invention may have a protein tag 602 bound thereto.

In the present invention, the protein tag may be one or more selected from the group consisting of biotin, calmodulin, FLAG, His, Myc, and streptavidin binding protein (SBP), and preferably, may be biotin, but is not limited thereto.

Signal Mediator Molecule:

It corresponds to a constituent that specifically binds to the second probe and results in a redox reaction so as to generate an electric current, thereby making it possible to confirm whether or not a target substance is present.

In the present invention, the signal mediator molecule 700 may include all of the substances 702 in which a substance capable of generating an electric current through a redox reaction is bound to the protein 701 that binds directly to the second probe or specifically binds to the protein tag of the second probe. Preferably, if the protein tag is biotin, it may be a substance in which horseradish peroxidase is bound to streptavidin, one molecule of which can bind to one molecule of biotin. In this way, if a signal mediator molecule in which horseradish peroxidase is bound to streptavidin capable of binding to biotin 1:1 is included, it is possible to significantly increase the sensitivity and accuracy in quantitative measurements of the target substance by specifically binding to the second probe bound to the target substance.

In another implementation of the present invention,
  there is provided a method of detecting a target substance in a sample using an electrochemical biosensor, wherein the electrochemical biosensor comprises, on a substrate, an electrode in which one or more wells for accommodating a sample are formed, a first probe provided at a bottom portion of the well, and an adaptor protein that specifically binds to the first probe, the method comprising:
  a) placing and reacting a biological sample separated from an object in the electrochemical biosensor; b) providing and reacting a second probe targeting a target substance to the well; c) reacting a signal mediator molecule targeting a substance tag bound to the second probe to the well; and d) by the reaction between the second probe and the signal mediator molecule in said step c) in the presence of an electrolyte, measuring an electric current generated by a redox reaction.

The "target substance" in the present invention may be a protein or peptide for measurement contained in a biological sample separated from an intended object. For the purposes of the present invention, the target substance may be a cytokine protein, which is a protein contained in a very small amount in a sample, and preferably, the cytokine protein may be interleukin, TGF-alpha, TGF-beta, interleukin-4, interleukin-6, MCP-1, interleukin-1-beta, interleukin-17, IFN-gamma, or the like.

The "intended object" of the present invention refers to an object for measuring the presence or a quantitative value of a target substance in a sample. Further, the "biological sample" obtained from the object in the present invention includes samples such as tissues, tissue lysates, bronchoalveolar lavage fluids, cells, blood, serum, plasma, saliva, sputum, cerebrospinal fluid, feces, or urine, etc. in which genes, proteins, and/or microRNAs, and the like corresponding to the target substance in accordance with the present invention are present, and includes any type of samples as long as they contain such a target substance to be measured.

In one embodiment of the present invention, in said step c), the reaction between the second probe and the signal mediator molecule can measure the electric current generated by a redox reaction in the presence of an electrolyte. Preferably, the electrolyte may comprise one or more of (3,3',5,5'-Tetramethylbenzidine), ECL (Enhanced chemiluminescence), and hydroquinone, and more preferably, may be TMB, but is not limited thereto. In this way, if the reaction between the second probe and the signal mediator molecule measures the current generated by electrons generated through the redox reaction in the presence of an electrolyte, it is possible to simplify the sensor since an AC constant-voltage device is not additionally required compared to the conventionally used impedance measurement method and to significantly improve the measurement limit and sensitivity, allowing the detection of a target substance corresponding to fg/ml.

Moreover, in the present invention, the first probe to be contained in the wells may be provided in such a way that different probes are contained in each of the wells, thereby allowing the simultaneous detection of various target substances through a single process.

In another aspect, yet another implementation of the present invention provides a method of manufacturing a biosensor comprising: modifying a surface of the electrode; forming one or more wells on the electrode; and binding an adaptor protein and a first probe to the modified electrode.

The details of the electrode, the first probe, the adaptor protein, and the second probe in the method of manufacturing a biosensor of the present invention are substantially the same as those described in the biosensor, and thus, the detailed descriptions thereof will not be repeated.

EMBODIMENTS

Hereinafter, the present invention will be described in greater detail through specific embodiments. The following embodiments are merely examples to help understand the present invention, and the scope of the present invention is not limited thereto.

[Production Example] Manufacture of Biosensor

Referring to the method for forming nanowells described in Journal of Biotechnology 168, 584-588, 2013, a plurality of nanowells having a diameter of 300 to 400 nm were formed in an array type on a surface of a gold electrode using a laser (see FIG. 1).

In particular, the electrode was formed in such a way that a silicon oxide film was formed (10 nm) on a 2×4 mm silicon wafer by plasma chemical vapor deposition, and an Au layer, which is a material that conducts electricity well and is a bio-friendly metal, was formed to a thickness of 50 nm by the e-beam evaporation method. In order to form fine nanowells on the Au layer created as such, a lithography method, which is a semiconductor process, was applied. For this purpose, a first photosensitive layer (PR, photoresist) was first applied and formed in 1 um. The thickness of the coating layer was formed in 100 nm in consideration of the etching selectivity because if too thin, it is not easy to form fine patterns, and if too thick, it cannot be completely removed after completion of the process. After forming the PR layer in this way, an E-beam lithography process was used to form fine patterns of a circular structure having a diameter of 200 nm. At this time, it is possible to adjust the diameter of the circular structure from nano- to micro-size according to the magnitude of e-beam power. In order to remove the PR (Zeon Corporation, Japan) and the insulating layer remaining after the etching (lithography) process is finished, the electrode formed was immersed in acetone (ACETON) and then removed using ultrasonic waves. The electrode produced as such was vacuum-packed individually to prevent oxidation, stored in a thermo-hygrostat, and washed in deionized water immediately before use.

Figure 4:
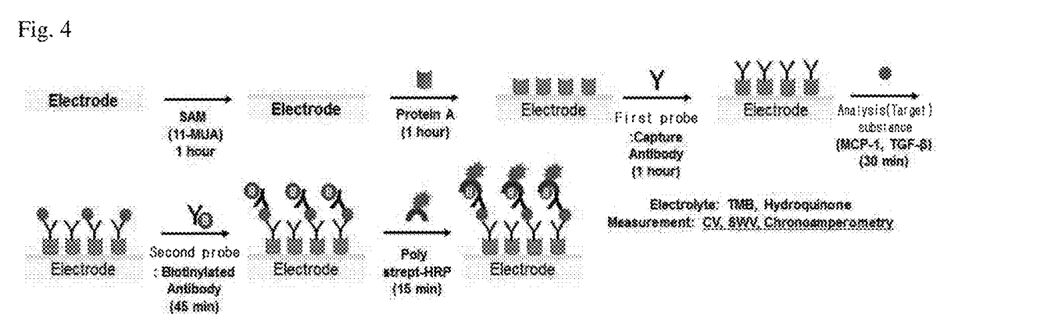
FIG. 4 shows a process of manufacturing a biosensor and detection thereof in accordance with an embodiment of the present invention.

Thereafter, the surface inside the wells formed on the gold electrode was hydrophilicized, and a reaction was carried out for one hour using 11-mercaptoundecanoic acid to modify into a self-assembled monolayer (SAM) in order to improve safety, reproducibility, and sensitivity in inducing covalent bonds with proteins, and the like, as shown in FIG. 4. Then, a reaction was carried out using 1M of ethanolamine for 10 minutes, so as to remove the material of the self-assembled monolayer that had not gone through the reaction. For immobilization of the antibody, protein A corresponding to an adaptor protein was bound to the gold electrode having a large number of modified wells obtained as above. Thereafter, a first probe, which is an antibody that specifically binds to the target substance to be measured, was reacted with said protein A for 1 hour to induce binding, thereby forming an electrode.

Further, a second probe that directly binds to the target substance was prepared by biotinlyation, and a substance in which HRP (horse peroxidase) is bound to streptavidin was prepared as a signal mediator molecule that binds to biotin bound to the second probe, and then was used for measurement using a biosensor.

[Experimental Example 1 and Comparative Example 1] Measurement of Target Substance Using Biosensor and Comparison with ELISA Method A biosensor in which the first probe and the second probe were prepared using antibodies specific for MCP-1 (purchased from R&D Systems) was used.

Figure 5:
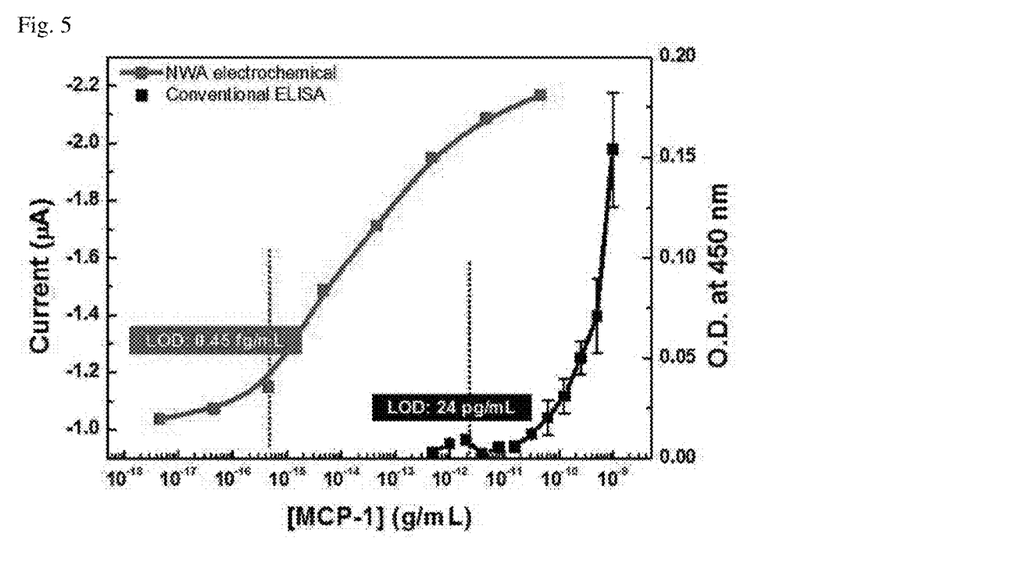
FIG. 5 shows a graph of measurement of MCP-1 protein using the ELISA and a biosensor in accordance with an embodiment of the present invention.

Each of the first probes was bound to each nanowell, and then reacted with 1 mg/ml of BSA for 30 minutes to prevent non-specific binding. Thereafter, MCP-1 protein, which is an antigen corresponding to the antibody of each of the first probes, was placed in each of the well and allowed to react for 30 minutes. Next, it was reacted with the biotinylated second probe for 45 minutes, and reacted with the signal mediator molecule in which HRP was bound to streptavidin for 15 minutes. Thereafter, a TMB solution corresponding to an electrolyte was added, and then the electric current was measured over time, the results of which are shown in FIG. 5. Here, the ELISA method was measured by a known typical method using the MCP-1 antigen and an antibody specific thereto.

As shown in FIG. 5, the measurement limit corresponded to $10^{-17}$ g/ml and it was possible to measure a wide range of concentration from $10^{-17}$ to $10^{-11}$ when measured with the biosensor in accordance with the present invention, whereas in the case of the ELISA method, the measurement limit was $10^{-12}$ g/ml, and the measurement was within a relatively narrow range of concentration of $10^{-9}$ g/ml.

From the above results, it can be seen that the biosensor in accordance with the present invention has the effect of not only being able to detect a very small amount of protein (a sample consumption amount of 5 ul or less) but also being capable of measuring a concentration corresponding to a wide range.

[Comparative Example 2] Comparison of Sensitivity Between Biosensors with Nanowell Electrode and Common Electrode The sensitivity was compared between an electrode having wells in accordance with the present invention, in particular, wells of a nano-sized diameter and an electrode without such wells.

Figure 6:
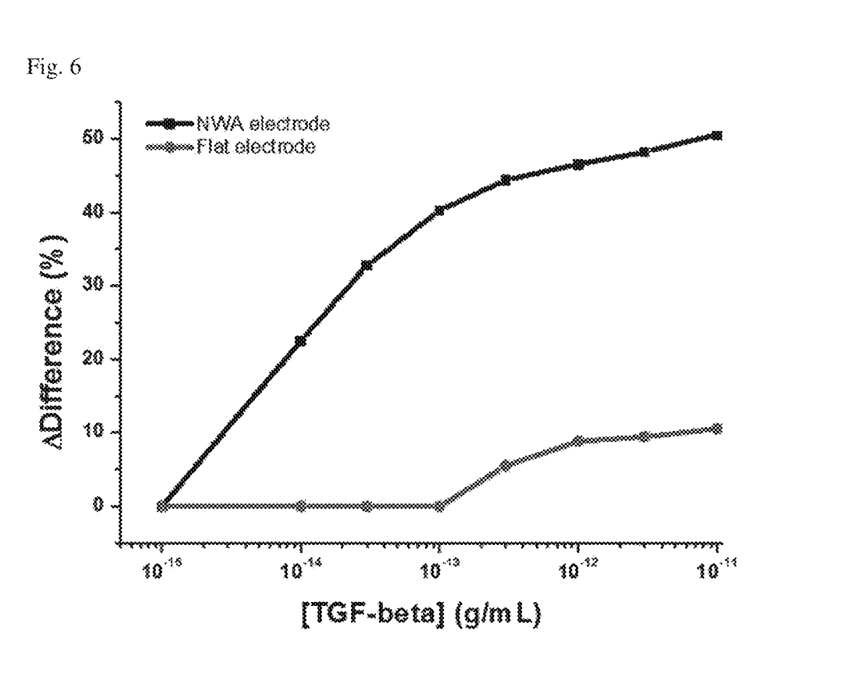
FIG. 6 shows a graph of measurement of the amount of TGF-beta using a flat electrode and a nanowell biosensor in accordance with an embodiment of the present invention.

Using the biosensor of Production Example 1 above having a nano-sized diameter in accordance with the present invention, and a sensor for measuring by fixing a probe to a flat electrode that does not contain wells and can be used in general, TGF-beta was measured as in Experimental Example 1 and Comparative Example 1 above, and the results are shown in FIG. 6.

As shown in FIG. 6, the difference in electric current increases proportionally as the amount of protein of TGF-beta increases in the case of the biosensor of Production Example 1 having a nano-sized diameter, whereas in the flat electrode, there was no change in the difference in electric current between $10^{-15}$ and $10^{-13}$ g/ml.

From the above results, it can be seen that the biosensor in accordance with the present invention has a significantly higher sensitivity in distinguishing lower concentrations compared to the case with a flat electrode.

[Comparative Example 3] Comparison of Measurements of Sensitivity (Specificity) Between Target Substances Using the biosensor in accordance with the present invention, a signal that specifically detected only selective antigens was confirmed.

Figure 7:
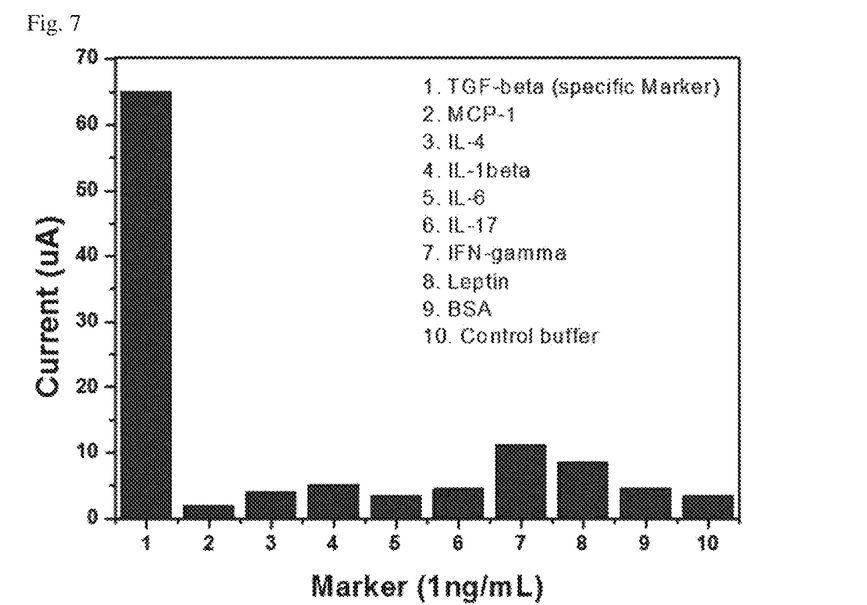
FIG. 7 shows a graph of measurement of the electric current generated per 1 ng/ml of various proteins using a nanowell biosensor (TGF-beta) in accordance with an embodiment of the present invention.

An antibody specific for TGF-beta (purchased from R&D Systems) was used as the first probe in the biosensor of Production Example 1 above, and MCP-1, IL-4, IL-1 beta, IL-6, IL-17, INF-gamma and Leptin, BSA, and a buffer were used as a control group, to treat a concentration of 1 ng/ml, respectively, and then the electric current generated was measured and shown in FIG. 7.

As shown in FIG. 7, other antigens exhibited a current intensity of about 10 uA, whereas TGF-beta exhibited a current intensity of 65 uA at 1 ng/ml.

Figure 8:
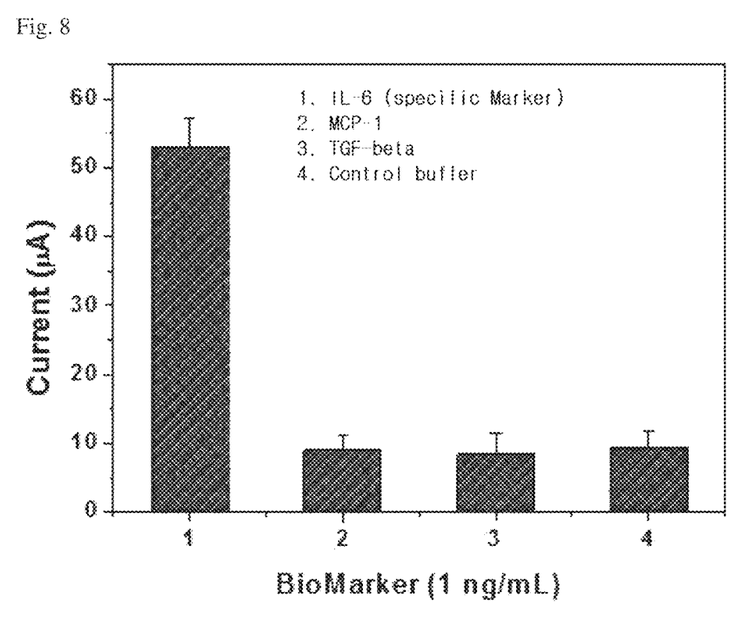
FIG. 8 shows a graph of measurement of the electric current generated per 1 ng/ml of various proteins using a nanowell biosensor (IL-6) in accordance with an embodiment of the present invention.

In addition, it was confirmed that even when the electrode was coated with another specific antibody, only the protein that specifically binds to that antibody showed a large change in the current intensity. In a similar way, as shown in FIG. 8, as a result of treatment at 1 ng/ml by using an antibody specific for IL-6 (purchased from R&D Systems), and using MCP-1, TGF-beta, and a buffer, it was confirmed that only the protein, that is, IL-6, exhibited a specifically large change in the current intensity.

Figure 9:
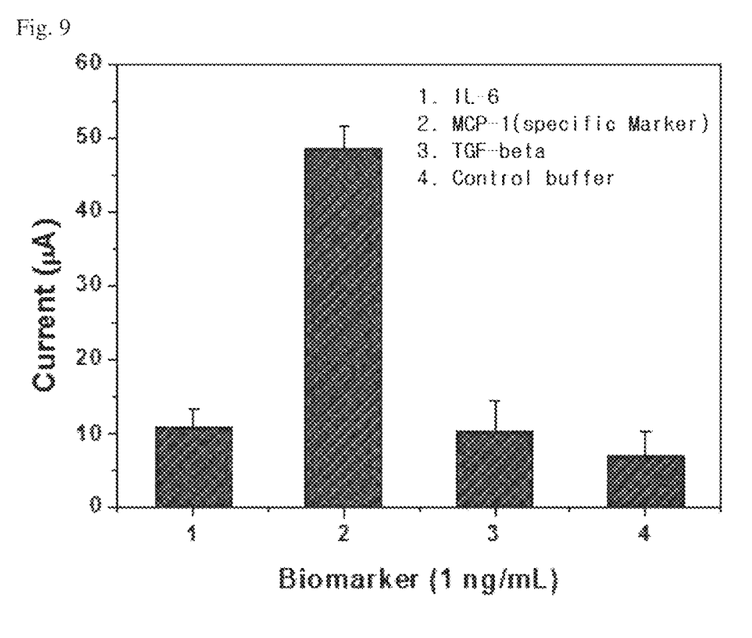
FIG. 9 shows a graph of measurement of the electric current generated per 1 ng/ml of various proteins using a nanowell biosensor (MCP-1) in accordance with an embodiment of the present invention.

As shown in FIG. 9 as well, as a result of treatment at 1 ng/ml by using an antibody specific for MCP-1 (purchased from R&D Systems), and using IL-6, TGF-beta, and a buffer, it was confirmed that only the protein, that is, MCP-1, exhibited a specifically large change in the current intensity.

[Experimental Example 2] Creating Calibration Curve

Figure 10:
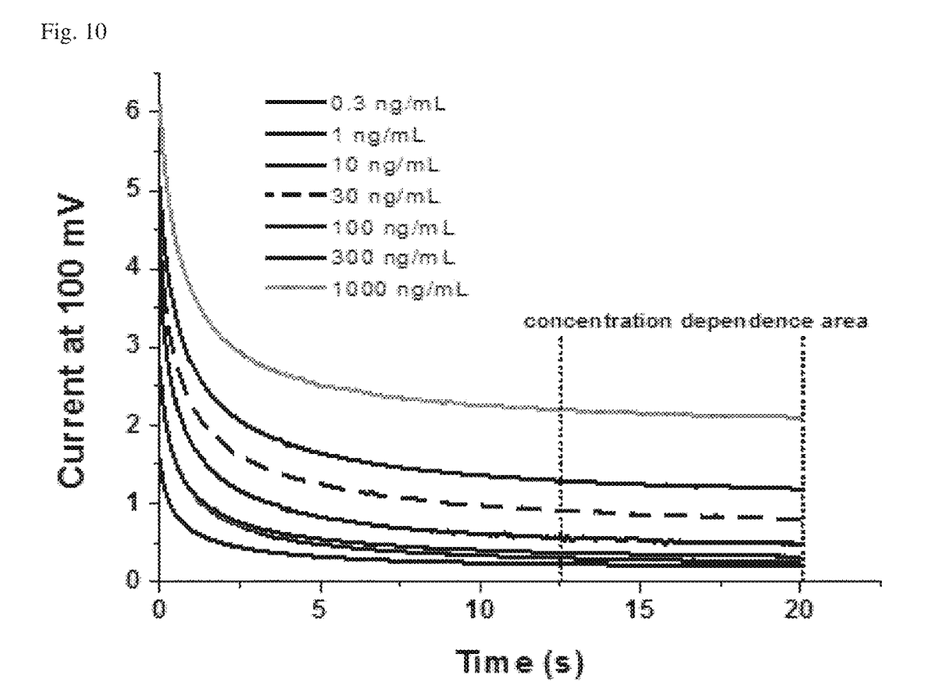
FIG. 10 shows a graph obtained by performing chronoamperometry by concentration in a PBS buffer using total immunoglobulin E (IgE) as a marker.
Figure 11:
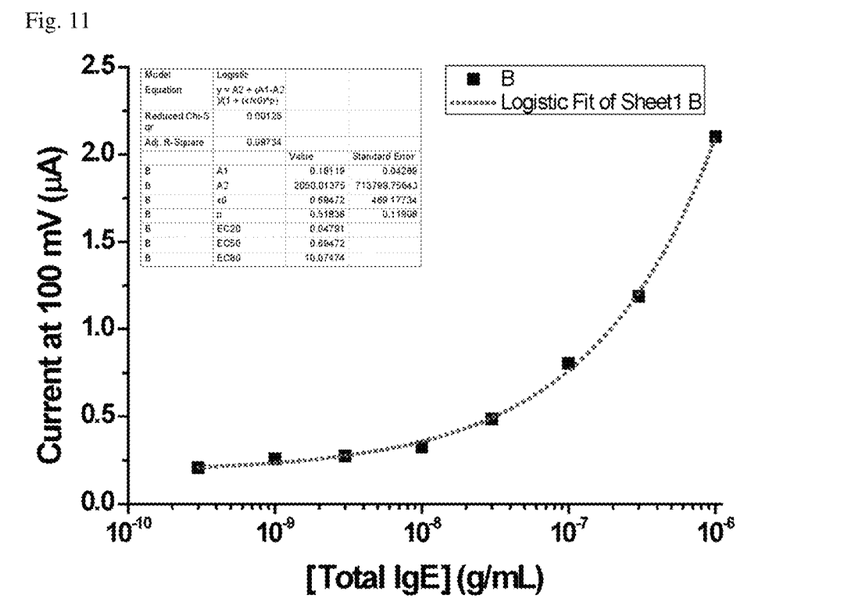
FIG. 11 shows a calibration curve representing an exponential curve in the range of pg to ng, created by calculating electric current values according to the total IgE concentrations.

The marker used to create a calibration curve is total immunoglobulin E (IgE), and IgE is a protein whose level increases rapidly in an inflammatory injury model. First, chronoamperometry was performed for each concentration in a PBS buffer for the quantification of IgE (FIG. 10), and accordingly, electric current values according to each concentration were calculated, thereby completing a calibration curve. As a result, it was confirmed that an exponential curve fitted to the range of pg to ng (FIG. 11).

[Comparative Example 4] Comparison of Measurement of IgE or IL-4 in Control Group (Untreated Group) and OVA (Ovalbumin) Administered Group Based on the quantification of the calibration curve completed in Experimental Example 2 above, the total IgE level was measured in an actual mouse model. In the case of the conventional ELISA method, a large amount of sample (e.g., blood) of about 100 to 200 μl was needed, which in turn led to an inevitable sacrifice of animals (mice) during measurement, and an impossibility of continuous monitoring, whereas the biosensor of the present invention exhibits a sensitivity in the order of fg/ml and can effectively detect a target protein from a very small amount of sample obtained without sacrificing animals, thereby allowing continuous monitoring as well.

Figure 12:
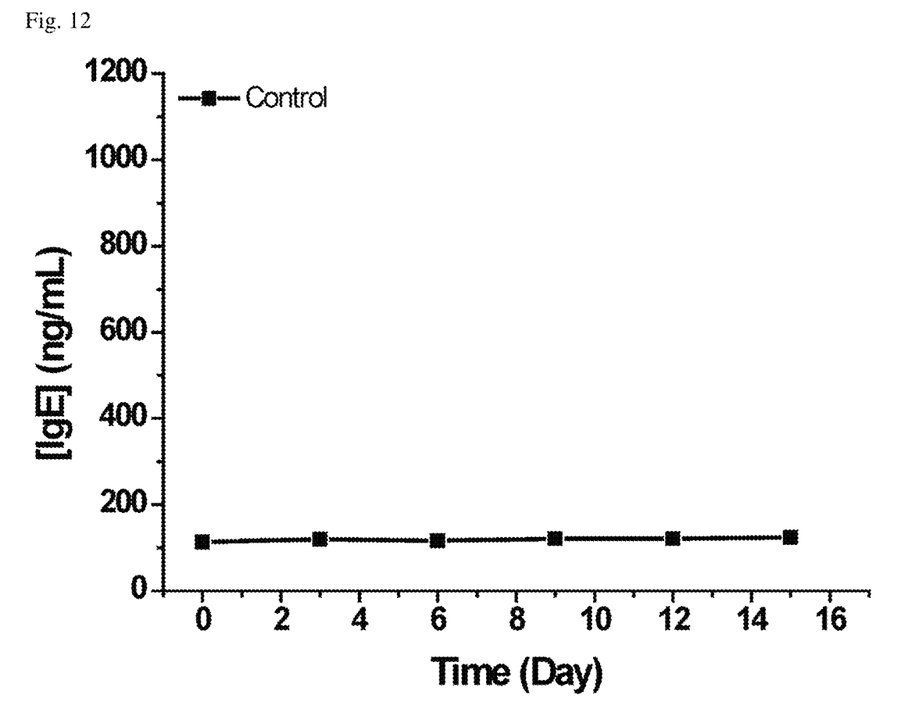
FIG. 12 shows the results obtained by measuring IgE levels over time for the mice in the control group (untreated group) using the biosensor of the present invention.
Figure 13:
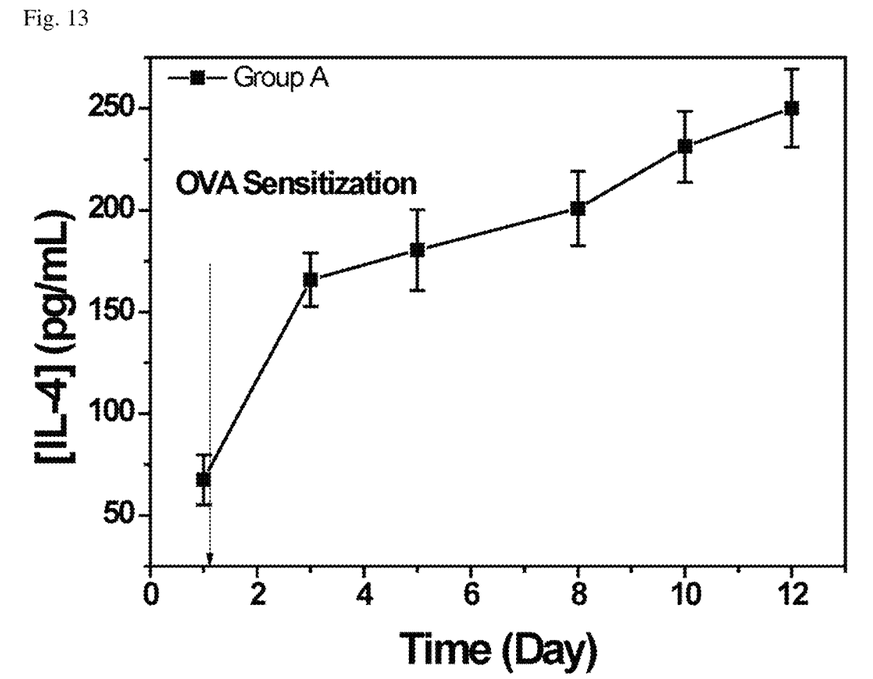
FIG. 13 shows the results obtained by measuring changes in cytokine IL-4 at intervals of two days using the biosensor of the present invention in the experimental group in which OVA (Ovalbumin) was sensitized and inhaled to induce asthma and airway inflammation.
Figure 14:
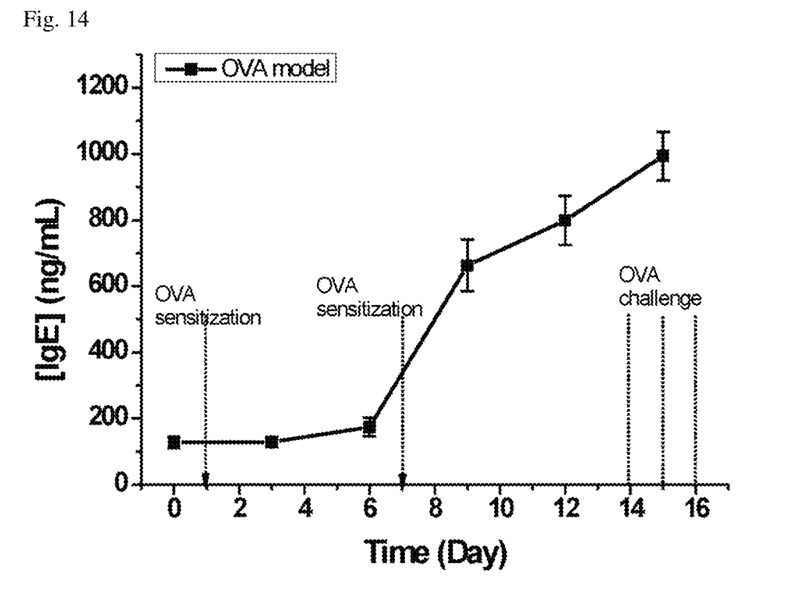
FIG. 14 shows the results obtained by measuring changes in cytokine IgE at intervals of two days using the biosensor of the present invention in the experimental group in which OVA was sensitized and inhaled to induce asthma and airway inflammation.

First, as a result of measuring the level of IgE using the biosensor and the detection method of the present invention for the mice in an untreated control group, it was confirmed that there was no difference in the IgE concentration over time through continuous monitoring (FIG. 12). On the other hand, in the case of the experimental group, OVA (Ovalbumin) was sensitized with a drug dropper and inhaled to induce asthma and airway inflammation, and changes in IL-4 and IgE, which are representative cytokines that increase correspondingly, were confirmed at intervals of two days. As a result, the biosensor of the present invention was able to accurately confirm the level of change and the progress of IL-4 and IgE concentrations over time (FIGS. 13 and 14), which is a result showing that continuous monitoring according to the increased sensitivity is possible, unlike the existing ELISA method, While the embodiments of the present invention have been described in detail above, the scope of the present invention is not limited thereto, and it will be apparent to those having ordinary skill in the art that various modifications and changes can be made without departing from the spirit of the present invention as set forth in the claims.

DESCRIPTION OF REFERENCE NUMERALS AND SYMBOLS

100: Electrode
200: Modified layer
300: Adaptor protein
400: First probe
500: Target protein

600: Second probe to which a protein tag is bound
601: Second probe
602: Protein tag
700: Signal mediator molecule to which peroxidase is bound
701: Protein that specifically binds to a protein tag
702: Substance capable of generating electric current through redox reaction (e.g., peroxidase)

What is claimed is:

1. An electrochemical amperometric biosensor comprising:
   an electrode in which one or more nano-wells for accommodating a sample are formed, wherein a diameter of the one or more nano-wells is from 300 nm to 400 nm;
   a first probe provided on the electrode and an adaptor protein that specifically binds to the first probe, wherein the adaptor protein is immobilized on the electrode exposed at a bottom portion of the nano-well;
   a second probe that specifically binds to a target substance that binds to the first probe; and
   a signal mediator molecule that specifically binds to the second probe,
   wherein the second probe is bound to a protein tag;
   wherein the electrode before the first probe is provided is surface-modified into a self-assembled monolayer (SAM);
   wherein the first probe specifically binds to the adaptor protein immobilized on the electrode exposed at the bottom portion of the nano-well;
   wherein the signal mediator comprises a protein that specifically binds to the protein tag and a peroxidase; and
   wherein the biosensor is configured to measure a concentration of the target substance in the sample by an amperometry method.

2. The electrochemical amperometric biosensor of claim 1, wherein the protein tag is one or more selected from the group consisting of biotin, calmodulin, FLAG, His, Myc, and streptavidin binding protein.

3. The electrochemical amperometric biosensor of claim 1, wherein the target substance is a protein or peptide.

4. The electrochemical amperometric biosensor of claim 1 having a sensitivity to the target substance on the order of femtogram per milliliter.

5. A method of detecting a target substance in a sample using an electrochemical amperometric biosensor,
   wherein the electrochemical amperometric biosensor comprises an electrode in which one or more nano-wells for accommodating a sample are formed, wherein a diameter of the one or more nano-wells is from 300 nm to 400 nm, a first probe provided at a bottom portion of the nano-well, and an adaptor protein that specifically binds to the first probe,
   the method comprising:
   a) placing and reacting a biological sample in the electrochemical amperometric biosensor;
   b) providing and reacting a second probe that binds to a target substance in the biological sample;
   c) providing and reacting a substance tag to the second probe;
   d) providing and reacting a signal mediator molecule that binds to the substance tag bound to the second probe;
   e) by the reaction between the second probe and the signal mediator molecule in said step d) in the presence of an electrolyte, measuring an electric current generated by a redox reaction, and
   f) measuring a concentration of the target substance in the sample by an amperometry method,
   wherein the adaptor protein is immobilized on the electrode exposed at a bottom portion of the nano-well;
   wherein the first probe specifically binds to the adaptor protein immobilized on the electrode exposed at the bottom portion of the nano-well;
   wherein the signal mediator comprises a protein that specifically binds to the substance tag and a peroxidase; and
   wherein the electrode before the first probe is provided is surface-modified into a self-assembled monolayer (SAM).

6. The method of claim 5, wherein the electrolyte comprises 3,3′,5,5′-tetramethylbenzidine, hydroquinone, or a combination thereof.

* * * * *